United States Patent [19]
Glickman

[11] Patent Number: 5,817,046
[45] Date of Patent: Oct. 6, 1998

[54] APPARATUS AND METHOD FOR ISOLATED PELVIC PERFUSION

[75] Inventor: Morton G. Glickman, New Haven, Conn.

[73] Assignee: Delcath Systems, Inc., Stamford, Conn.

[21] Appl. No.: 891,745

[22] Filed: Jul. 14, 1997

[51] Int. Cl.⁶ .................................................. A61M 35/00
[52] U.S. Cl. ............................................. 604/4; 604/158
[58] Field of Search .................................. 604/4–6, 158, 604/161, 164–165, 48, 49, 43–47, 51, 53

[56] References Cited

U.S. PATENT DOCUMENTS

| | | |
|---|---|---|
| Re. 28,742 | 3/1976 | Rafferty et al. . |
| 2,642,874 | 6/1953 | Keeling . |
| 3,045,677 | 7/1962 | Wallace . |
| 3,411,506 | 11/1968 | Velasco . |
| 3,516,408 | 6/1970 | Montanti . |
| 3,647,324 | 3/1972 | Rafferty et al. . |
| 3,811,800 | 5/1974 | Shill . |
| 3,837,347 | 9/1974 | Tower . |
| 3,851,649 | 12/1974 | Villari . |
| 3,864,055 | 2/1975 | Kletschka et al. . |
| 3,888,250 | 6/1975 | Hill . |
| 3,957,389 | 5/1976 | Rafferty et al. . |
| 3,959,128 | 5/1976 | Harris . |
| 3,970,408 | 7/1976 | Rafferty et al. . |
| 3,995,617 | 12/1976 | Watkins et al. . |
| 4,013,564 | 3/1977 | Nose . |
| 4,037,984 | 7/1977 | Rafferty et al. . |
| 4,047,526 | 9/1977 | Reynolds et al. . |
| 4,048,064 | 9/1977 | Clark, III . |
| 4,059,512 | 11/1977 | Harris . |
| 4,127,481 | 11/1978 | Malchesky et al. . |
| 4,140,652 | 2/1979 | Korshak et al. . |
| 4,171,283 | 10/1979 | Nakashima et al. . |
| 4,183,811 | 1/1980 | Walch et al. . |
| 4,192,302 | 3/1980 | Boddie . |
| 4,206,050 | 6/1980 | Walch et al. . |
| 4,218,321 | 8/1980 | Sasaki et al. . |
| 4,231,366 | 11/1980 | Schael . |
| 4,250,141 | 2/1981 | Lehmann et al. . |
| 4,300,550 | 11/1981 | Gandi et al. . |
| 4,300,551 | 11/1981 | Kinney . |
| 4,303,521 | 12/1981 | Lehmann . |

(List continued on next page.)

FOREIGN PATENT DOCUMENTS

| | | |
|---|---|---|
| 0 119 596 | 9/1984 | European Pat. Off. . |
| 0 185 865 | 7/1986 | European Pat. Off. . |
| 0 228 532 | 7/1987 | European Pat. Off. . |
| 28 34 956 | 2/1980 | Germany . |
| 511951 | 6/1976 | U.S.S.R. . |
| 651-817 | 3/1979 | U.S.S.R. . |
| WO 88/06045 | 8/1988 | WIPO . |

OTHER PUBLICATIONS

V. Wizemann et al., *Portocaval Hemofiltration During the Anhepatic Phase.* . . , pp. 485–487.
Pierre M. Galletti et al., *Hemodialysis in Cancer Chemotherapy*, pp. 20–24.
Michael W. Horton et al., *Continuous Arteriovenous Hemofiltration.* . . , pp. 1361–1368.
Sadao Kamidono et al., *A Fundamental Study of Regional Chemotherapy.* . . , pp. 176–178.
Winchester et al., *Dialysis and Hemoperfusion of Poisons and Drugs*, p. 787.
Yukihiko Nose et al., *Therapeutic Apheresis: A Critical Look*, pp. 93–175.
Tohru Tani et al., *new Anticancer Treatment by Hemoperfusion.* . . , pp. 202–240.
Robert K. Ausman, *Development of a Technic for Isolated Perfusion of the Liver*, pp. 3993–3997.

*Primary Examiner*—John G. Weiss
*Assistant Examiner*—Ki Yong O
*Attorney, Agent, or Firm*—Stephen E. Feldman

[57] ABSTRACT

The instant invention provides a novel apparatus, kit and process for isolating a flow circuit within the pelvic cavity of a patient for perfusing a high concentration of a chemotherapeutic agent therethrough, without contaminating the blood circulating in the substantial remainder of the patient's blood circulatory system with the agent.

12 Claims, 4 Drawing Sheets

U.S. PATENT DOCUMENTS

| | | |
|---|---|---|
| 4,313,831 | 2/1982 | Lehmann et al. . |
| 4,376,707 | 3/1983 | Lehmann . |
| 4,385,631 | 5/1983 | Uthmann . |
| 4,416,280 | 11/1983 | Carpentar et al. . |
| 4,423,725 | 1/1984 | Baran et al. . |
| 4,445,892 | 5/1984 | Hussein et al. . |
| 4,500,309 | 2/1985 | Diederich et al. . |
| 4,540,402 | 9/1985 | Aigner . |
| 4,546,759 | 10/1985 | Solar . |
| 4,563,170 | 1/1986 | Aigner . |
| 4,573,966 | 3/1986 | Weikl et al. . |
| 4,609,461 | 9/1986 | Takata et al. . |
| 4,610,662 | 9/1986 | Weikl et al. . |
| 4,634,604 | 1/1987 | Tlustakova et al. . |
| 4,636,195 | 1/1987 | Wolinsky . |
| 4,648,865 | 3/1987 | Aigner . |
| 4,655,746 | 4/1987 | Daniels et al. . |
| 4,666,426 | 5/1987 | Aigner . |
| 4,681,764 | 7/1987 | Endo et al. . |
| 4,696,668 | 9/1987 | Wilcox . |
| 4,705,502 | 11/1987 | Patel . |
| 4,708,718 | 11/1987 | Daniels . |
| 4,714,460 | 12/1987 | Calderon . |
| 4,728,432 | 3/1988 | Sugiyama et al. . |
| 4,731,055 | 3/1988 | Melinyshyn et al. . |
| 4,741,328 | 5/1988 | Gabbay . |
| 4,744,366 | 5/1988 | Jang . |
| 4,781,677 | 11/1988 | Wilcox . |
| 4,820,261 | 4/1989 | Schmoll et al. . |
| 4,828,882 | 5/1989 | Tsezos et al. . |
| 4,832,034 | 5/1989 | Pizziconi et al. . |
| 4,832,839 | 5/1989 | Tamura . |
| 4,867,742 | 9/1989 | Calderon . |
| 4,883,459 | 11/1989 | Calderon . |
| 5,186,712 | 2/1993 | Kelso et al. ............................ 604/165 |
| 5,609,598 | 3/1997 | Laufer et al. ........................... 606/142 |

ISOLATED PELVIC PERFUSION

ISOLATED PELVIC PERFUSION

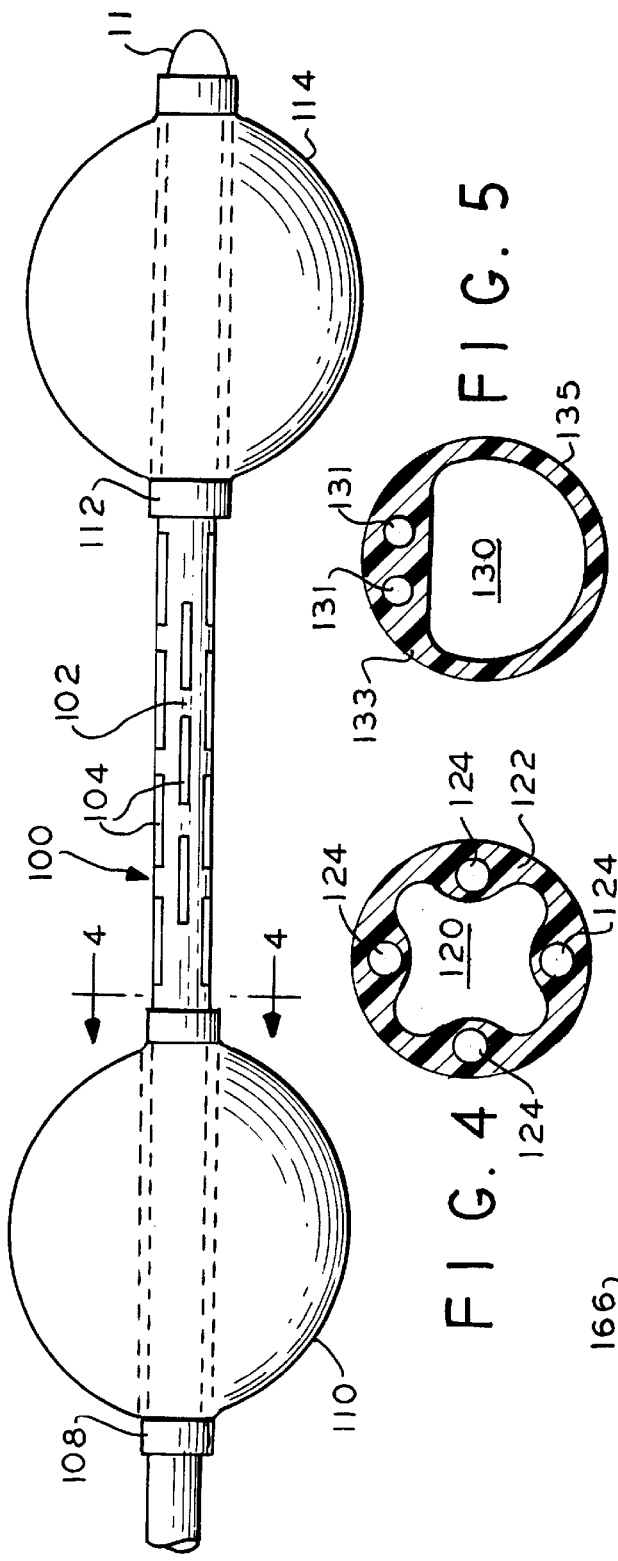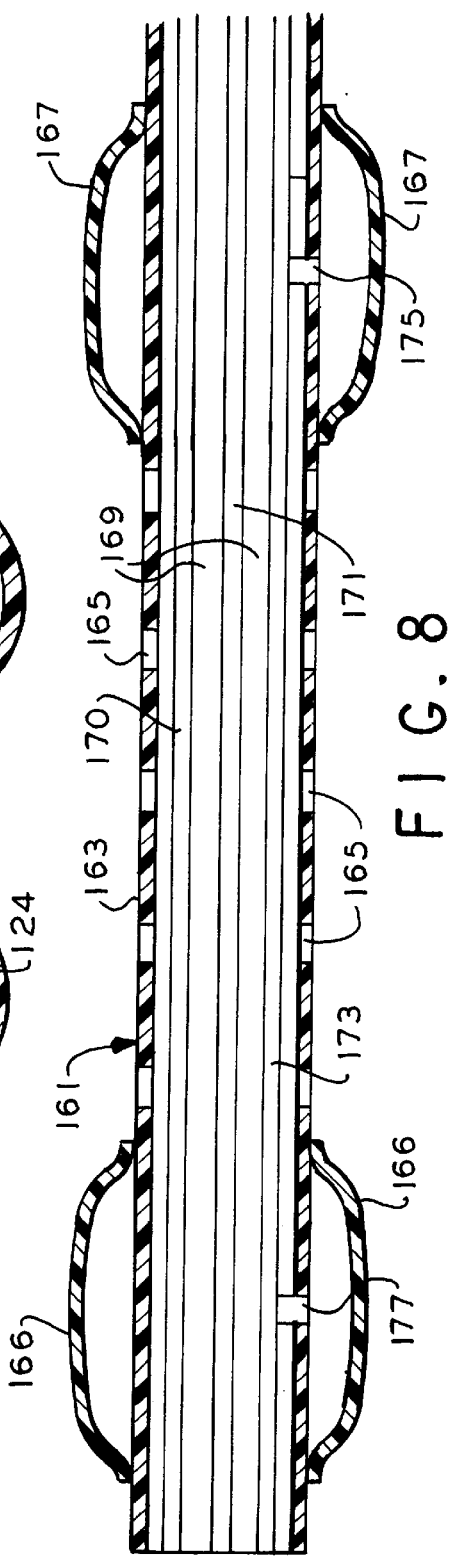

APPARATUS AND METHOD FOR ISOLATED PELVIC PERFUSION

BACKGROUND OF THE INVENTION

The instant invention relates to the treatment of tumors in the body of a patient inflicted with cancer. More specifically, the invention relates to the chemotherapy treatment of tumors in the body of a patient inflicted with cancer. Still more specifically the invention relates to the treatment by chemotherapy of tumors in the pelvic cavity of the body of a patient inflicted with cancer Chemotherapy is the treatment of disease using chemical agents that are intended to eliminate the causative organism without harming the patient. In the strict sense, this applies to the use of antibiotics to treat such invading organisms as bacteria, viruses, fungi, or parasites. The term is commonly used, however, to describe the use of drugs to treat cancer, in which case the target is not a causative organism but wildly multiplying cells. The purpose of the therapy is to selectively kill tumor cells and leave normal cells unharmed—a very difficult task because drugs have a narrow therapeutic zone beyond which they harm normal cells as well as cancer cells. Approximately 50 different anticancer drugs are available, and an equal number are currently being tested. Anticancer drugs are only relatively selective for cancer cells, and the toughest task for the physician is to select a drug that will destroy the most cancer cells, leave normal cells unharmed, and cause the fewest unpleasant and undesirable side effects. The therapeutic goal is to favorably balance the risk-benefit ratio in which the morbidity of the treatment is weighed against its potential benefits. If a treatment causes patients to be miserable and has only a slight chance of prolonging life, many patients will forego further treatment. However, if the potential for significantly prolonging survival by aggressive therapy exists, the patient may decide to continue with the therapy.

Prior to the instant invention, chemotherapy has not been a particularly effective mode of treating tumors occurring in the pelvic cavity.

Thus it is the primary object of the instant invention to provide a novel apparatus and process for the localized perfusion of a high concentration of an anti-cancer agent through a tumor occurring the pelvic cavity of a patient, without substantially contaminating the blood circulating in the substantial remainder of the patient's blood circulatory system with the agent. The invention enables the by-pass of the contaminated blood through an extracorporeal circuit which includes a scheme for decontaminating the contaminated blood. After decontamination, the blood is thereafter infused back into the body of the patient at a point remote from where it was initially withdrawn. Thus, the invention prevents otherwise toxic levels of such agents from entering the substantial remainder of the patient's blood circulatory system; while at the same time, delivering doses of the agent which are substantially lethal only to the tumor. The improvement to the apparatus disclosed herein is applicable to a great variety of prior art apparatus hitherto used for conducting processes similar to that instantly disclosed.

U.S. Pat. No. 5,597,377, to Aldea teaches a catheter for retroperfusion of myocardium has an infusion tip, such that when retroperfusing myocardium, the tip extends within the coronary sinus to a depth in a range of about 2 to 4 inches (5 to 10 cm) from the coronary sinus ostium. The catheter also comprises a tube defining at least three channels. The channels include an infusion channel, which has a first infusion end coupled to an infusion port located in the infusion tip and a second infusion end coupled to an outlet orifice of a pump; a withdrawal channel, which has a first withdrawal end coupled to a withdrawal port located in the superior vena cava and a second withdrawal end coupled to an inlet orifice of the pump; and a pressure monitoring channel for monitoring pressure at pressure port at the infusion tip having a first monitoring end coupled to the pressure port and a second monitoring end coupled to a pressure sensor. The catheter also has a microprocessor for controlling the pump and measuring a rate of retroperfusate flow, whereby autologous venous blood entering the withdrawal port is continuously discharged at the infusion port at a flow rate in a range of about 5 to 50 mil./min. and at a pressure less than about 15 mm Hg. The tube and tip are made from biocompatible, non-thrombogenic material. Further, the catheter has remotely identifiable markers spaced along the tube, and a marker is located at said infusion tip. The invention also is a method for coronary sinus retroperfusion. The method includes the steps of inserting the catheter through the patient's jugular vein; guiding the catheter's infusion tip into the coronary sinus, such that when retroperfusing myocardium, the tip extends within the coronary sinus to a depth in a range of about 2 to 4 inches (5 to 10 cm) from the coronary sinus ostium; and providing a non-synchronized retroperfusate flow of autologous venous blood at a rate in a range of about 5 to 50 mil./min. and at a pressure less than about 15 mm Hg.

U.S. Pat. No. 5,569,182 Twardowski, et. al., teaches blood which is circulated through a multiple lumen catheter which connects between a vein of a patient and the blood treatment device. The catheter and the lumens thereof each define distal ends which are positioned within the vein. By this invention, one withdraws blood from the vein through one of the lumens at a flow rate of at least about 200 ml./min. while also inserting blood into the vein through another of said lumens at a similar flow rate. The distal ends of the lumens are longitudinally spaced from each other by no more than about 5 mm. It have been found that the following advantages can be achieved by this method: less clot formation coupled with low direct blood recirculation and longer catheter survival. Also, the catheter works well in either direction of blood flow through the respective lumens.

U.S. Pat. No. 5,509,897, to Twardowski, et. al., teaches a catheter for hemodialysis comprises a flexible catheter tube defining a plurality of separate lumens. The catheter defines an arc angle of generally U-shape in its natural, unstressed configuration. Thus, the catheter may be implanted with a distal catheter portion residing in a vein of the patient, the distal catheter portion being of substantially the shape of the vein in its natural, unstressed condition. Also, a proximal catheter portion resides in a surgically created tunnel extending from the vein and through the skin of the patient, this section of the Catheter also being typically in its natural, unstressed condition. Thus blood may be removed from the vein through one lumen of the catheter, and blood may be returned to the vein through another lumen of the catheter, while the catheter is subject to long term indwelling in the body. Improved results are achieved because of the lack of mechanical stress in the shape of the catheter, which stress causes the catheter to press unduly against adjacent tissues.

U.S. Pat. No. 5,505,698, to Booth, et. al., teaches a catheter for supplying liquid to the coronary sinus in a perfusion procedure comprising a tubular catheter body having an interior lumen, a proximal end, and a distal end; and an inflatable cuff (balloon) adjacent the distal end of the catheter. The cuff has a proximal end and a distal end, each of which encircle the catheter body and hermetically seal thereto. The cuff further comprises an elongated central section having a length of at least 1 inch. When the inflated cuff is positioned a sufficient distance into the coronary sinus to firmly retain the cuff therein, it blocks the left coronary vein where it meets the coronary sinus. Further, the cuff can comprise end panels defined between the central section and the proximal and distal cuff ends. The end panels have a shape which allows for flexure between the central section and the cuff's proximal and distal ends.

U.S. Pat. No. 5,489,274, to Chu, et. al., teaches an easy operating, durable closure device for controlling the closure of a passageway in for example valves and the like used in medical applications. The device includes a cam surface arranged about the circumference of a resilient tubing member. Rotation of the cam controls the radial position of a compression member that compresses the tubing member to effect closure. Such a closure device, or a two-part rotary closure device in general, is constructed to receive an accessory component such as a syringe, the rotary connecting movement of which automatically opens the closure device. The device may be used as a torqueable handle for a guidewire gripped in the passage. A large scale version of the device is joined to an introducer sheath, sized to pass an introducer catheter for e.g., a Green field filter, or to close upon a guidewire to prevent backflow of blood.

U.S. Pat. No. 5,462,529, to Simpson, et. al., teaches a catheter device for treatment of disease in biological conduits. The device has inner and outer coaxial catheter members, each having an inflatable balloon attached near its distal end. When the balloons are inflated, a sealed treatment chamber is created between the balloons. The length of the treatment chamber is adjustable by sliding the coaxial catheter members with respect to each other to obtain a desired separation between the attached balloons before inflation. Biological debris is trapped within the chamber and removed by infusion and aspiration of a flushing fluid, reducing the risk of myocardial infarction. Adjunctive treatment devices can be inserted into the sealed treatment chamber through a lumen of the outer coaxial member.

U.S. Pat. No. 5,458,583, to McNeely, et. al. A system and method for inserting a gastrostomy catheter through a passageway formed through the abdominal and stomach walls of a patient. The gastrostomy catheter is mounted onto a dilatation catheter with a dilatation member such as an inelastic balloon on the distal extremity thereof. An introducer needle is first advanced through the walls of the patient's abdomen and stomach into the interior of the stomach and then a guidewire is advanced through the inner lumen of the needle into the stomach interior. The gastrostomy catheter-dilatation catheter assembly is advanced over the guidewire until the balloon on the dilatation catheter is in proper position crossing both the abdominal and gastric walls. Upon inflation of the balloon on the dilatation catheter, the passageway is expanded enough so that the gastrostomy catheter can be advanced therethrough to dispose the distal end of the gastrostomy catheter within the interior of the stomach. The balloon on the distal end of the gastrostomy catheter is inflated so as to form an internal retention member and the catheter withdrawn in order to urge the inflated balloon against the stomach wall. Preferably, the gastrostomy catheter has an external retention ring on the shaft thereof which is slid against the exterior of the patient's abdomen to seal the passageway through the abdominal wall.

U.S. Pat. No. 5,423,745 to Todd, et. al., teaches balloon catheters for use in infusing a solution into a body passageway, and their methods of use and manufacture. Each catheter contains at least one lumen through which a solution flows into the body. The balloons of each catheter are secured to the proximal end of the catheter, and each have a plurality of protuberances projecting outwardly from the outer surface of the balloons for the purpose of firmly gripping the walls of the body passageway so as to secure placement of the catheter within the passageway. A malleable wire assists in retaining the catheter in position within the body passageway. A double balloon catheter allows sealing of the body passageway to be accomplished separately from securely gripping the walls.

U.S. Pat. No. 5,405,320, to Twardowski, et. al., teaches a catheter for hemodialysis comprises a flexible catheter tube defining a plurality of separate lumens. The catheter defines an arc angle of generally U-shape in its natural, unstressed configuration. Thus, the catheter may be implanted with a distal catheter portion residing in a vein of the patient, the distal catheter portion being of substantially the shape of the vein in its natural, unstressed condition. Also, a proximal catheter portion resides in a surgically created tunnel extending from the vein and through the skin of the patient, this section of the catheter also being typically in its natural, unstressed condition. Thus blood may be removed from the vein through one lumen of the catheter, and blood may be returned to the vein through another lumen of the catheter, while the catheter is subject to long term indwelling in the body. Improved results are achieved because of the lack of mechanical stress in the shape of the catheter, which stress causes the catheter to press unduly against adjacent tissues.

U.S. Pat. No. 5,398,687, to Abell, teaches new devices and methods for detecting and diagnosing motility abnormalities within the pancreaticobiliary tree. In the first device, a modified ERCP catheter with electrical activity sensing is positionable within the biliary tract, and operates to sense electrical activity during the ERCP procedure. Electrical activity is sensed by two circumferential leads formed by bands of silver, located near the distal tip of the catheter. The detection of electrical activity, in combination with the simultaneous radioscopic visualization of the biliary tract, provides a detailed motility profile for the physician without requiring the additional use of a perfusion catheter. A second device is also disclosed which detects motility within the biliary tract by the simultaneous sensing of electrical activity and surrounding fluid pressure. A biliary catheter has two circumferential silver leads and three perfusion lumens whose outlets are alternately spaced between the silver leads. When positioned within the biliary tract, this catheter yields valuable data correlating electrical activity and the corresponding occurrence of muscle activity. By the sequential detection of pressure changes at the proximal, medial, and distal perfusion outlets interspersed between the electrical activity leads, both the presence and direction of muscle activity are sensed in relation to the sensed electrical activity about the leads.

U.S. Pat. No. 5,397,310, to Chu, et. al., a catheter introducer sheath assembly, for introduction into a body passage of a catheter containing a filter comprises a flexible introducer sheath joined to the distal end of a closure device forming a through-passage with a diameter sufficient to pass the catheter therethrough. The closure device has a resilient member in the through-passage and two rotatable body portions, one stationary with respect to the resilient member, and the other rotatable about the axis of the resilient member with an internal cam circumferentially spaced around the axis. A compression member positioned radially in an extending aperture makes contact with both the resilient member and the cam surface to vary the through-passage allowing the operator to manually control the passage of the device. The sheath assembly receives a cathetory guidewire that slides through and extends beyond the closure device and the sheath. In another aspect, the combination sheath assembly and closure device forms a catheter introducer kit constructed to receive a stabilizer and a catheter of sufficiently large diameter to house a vena cava filter, and to pass the filter through the closure device and sheath for placement in the body by means of a dilator attached to the end of the sheath to facilitate guiding the filter to the desired position for its release from the sheath. The closure device is adjustable to prevent any backflow of fluid such as blood from the assembly during the filter placement procedure.

U.S. Pat. No. 5,397,307, to Goodin, teaches an intravascular material delivery dilation catheter having a pair of longitudinally spaced inflatable balloons with a drug delivery region defined therebetween. The catheter is ideally suited for use after a PTCA procedure, wherein the proximate balloon seals the blood vessel while the distal balloon is uniquely contoured when inflated to define fluid communication paths therepast and proximate a blood vessel to be treated. The distal balloon, when inflated, has four lobes but could also be textured. Each lobe is separated from the next by a groove, which groove in combination with the blood vessel inner wall forms a fluid communication path therebetween. Upon inflation of both balloons in a blood vessel, a medicament such as heparin can be injected, via the drug delivery region between the inflated balloons, wherein the medicament flows past the distal balloon at a selected rate. Accordingly, a medicament can be injected directly to a treatment site rather than injected as a bolus dose, thus, a smaller dosage may be employed to minimize side effects. Alternatively, perfusion can be accomplished by only partially inflating the proximate balloon to constrict flow therepast, or eliminating the proximate balloon entirely, where the drug delivery region is disposed upstream of the contoured distal balloon.

U.S. Pat. No. 5,370,614, to Amundson, et. al., teaches a balloon catheter includes a sheath surrounding the balloon, the sheath having a longitudinal line of weakness and a drug-containing viscous matrix material intermediate between the balloon and the sheath such that when the balloon is positioned and inflated in the body lumen it causes the sheath to burst at the line of weakness and release viscous matrix material onto said body lumen. The device provides accurate placement of the dosage required at the location in need of treatment. The catheter is especially useful in balloon angioplasty procedures.

U.S. Pat. No. 5,338,301, to Diaz, teaches an extendable balloon-on-a-wire catheter which includes a telescoping exchange core wire mounted along the inside lumen of the longitudinal tube of the balloon-on-a-wire assembly. In the preferred embodiment, the exchange core wire is mounted within a hypodermic tube secured to the core wire of the balloon-on-a-wire assembly. A multiple component system includes this balloon-on-a-wire assembly together with an over-the-wire catheter which slidably passes over the elongated body of the balloon-on-a-wire assembly. Preferably, the relative sizing of these components of the system is such that the over-the-wire catheter does not pass over the balloon of the balloon-on-a-wire assembly. In a treatment procedure, the balloon-on-a-wire assembly achieves dilation of a lesion or a stenosis, after which it is moved somewhat distally to clear the stenosis. When the over-the-wire catheter is used, it is slidably moved over the balloon-on-a-wire assembly until its treatment location reaches the stenosis. During the procedure, the exchange core wire can be telescopically extended to a length such that the surgeon can readily grasp the balloon-on-a-wire assembly or its exchange core wire during manipulation of the over-the-wire catheter.

U.S. Pat. No. 5,324,261, to Amundson, et. al., teaches a balloon catheter includes a sheath surrounding the balloon, the sheath having a longitudinal line of weakness and a drug-containing viscous matrix material intermediate between the balloon and the sheath such that when the balloon is positioned and inflated in the body lumen it causes the sheath to burst at the line of weakness and release viscous matrix material onto said body lumen. The device provides accurate placement of the dosage required at the location in need of treatment. The catheter is especially useful in balloon angioplasty procedures.

U.S. Pat. No. 5,304,121, to Sahatjian, teaches a catheter and methods for delivering drug to tissue at a desired location of the wall of a body lumen. The catheter is constructed for insertion in a body lumen and has a catheter shaft and an expandable portion mounted on the catheter shaft. The expandable portion is expandable to a controlled pressure to fill the cross-section of the body lumen and press against the wall of the body lumen. In one embodiment, at least a portion of the exterior surface of the expandable portion is defined by a coating of a tenaciously adhered swellable hydrogel polymer. Incorporated in the hydrogel polymer is an aqueous solution of a preselected drug to be delivered to the tissue or plaque. The hydrogel polymer and drug are selected to allow rapid release of a desired dosage of the drug from the hydrogel polymer coating during compression of the hydrogel polymer coating against the wall of the lumen when the expandable portion is expanded. In other embodiments the polymer is released from the expandable portion in response to pressure, to coat the wall of the body lumen.

U.S. Pat. No. 5,286,259, to Ganguly, et. al., teaches a catheter (10) having a stepped coaxial construction formed by and internal tube 12) and an external tube (14). The internal tube includes a distal pressure lumen (26), a balloon inflation lumen (28), and a sensor lumen (30). The external tube includes the first proximal pressure lumen (48), second proximal pressure lumen (50), injection lumen (52), and transducer lead lumen (54). A cylindrical transducer (16), sensor (18), and balloon (42) are supported on the internal and external tubes, which allow the transducer to be coaxially mounted thereon. The catheter has a high lumen count, large lumen cross-sectional area, is easy to construct and use, and allows cardiac output to be measured continuously without sacrificing other currently available catheter functions.

U.S. Pat. No. 5,281,200, to Corso, Jr., et. al., teaches a balloon catheter system which includes a balloon-on-a-wire assembly and an over-the-wire catheter which slidably passes over the elongated body of the balloon-on-a-wire assembly, but not over its balloon. In the procedure by which the system is used, the balloon-on-a-wire assembly achieves an initial dilation or predilation of a lesion or stenosis, after which it is moved somewhat distally to clear the predilated stenosis. The over-the-wire catheter then is slidably moved over the balloon-on-a-wire assembly until its balloon reaches and dilates the predilated stenosis. After dilation is completed, the system is removed from the body vessel thus treated.

U.S. Pat. No. 5,279,546, to Mische, et. al., teaches an apparatus and method for dissolving and removing material which tends to occlude a bodypassageway, such as an artery. The device employs a dual catheter system arranged in coaxial fashion. Each of the catheters has an inflatable balloon at its distal tip. Inflating the two balloons occludes the body passage way both proximal and distal to the treatment area, thus isolating it from fluid contact with the rest of the body. Because concentric catheters are used, the distance between the balloons and hence the size of the treatment area is adjustable. The thrombolytic agent is infused through orifices in the inner catheter in the region between the two balloons. A piezo electric device supplies ultrasonic agitation within the treatment area. A pressure device monitors the body passage way for unsafe conditions. Aspiration is accomplished through one or more lumens in the outer catheter. Ultrasonic agitation may be employed with the aspiration also to break up masses of material which may be too big to pass through the exit lumen cross section.

U.S. Pat. No. 5,254,089, to Wang, teaches an inflatable medical device for the delivery of medications to an organ in the body including acatheter having a plurality of lumens disposed therein. The distal end of the catheter is adapted to be disposed within a bodily organ. A hollow, inflatable, medication-deliverable balloon is disposed on the distal end of the catheter and the interior of the balloon is in fluid flow relationship with one of the lumens to enable the balloon to be inflated. An array of conduits is disposed within the walls of the balloon for the delivery of medications to predetermined locations within said bodily organ. Another lumen in the catheter shaft is provided to deliver medications to the conduits in the wall of the balloon and an egress for the medications so that they may be dispensed at the site being treated.

U.S. Pat. No. 5,236,417, to Wallis, teaches a cholangiography catheter for injecting dye into a cystic duct during laparoscopic cholangiography. The catheter includes a bifurcated connector having a length of tubing and a check valve mounted to each arm of the connector. A saline syringe is coupled to one check valve and a dye syringe is coupled to the other check valve. The check valves and respective syringes are color coordinated to preclude inadvertently using the wrong syringe. The catheter is fabricated from a medical grade polymer having a preselected degree of compliant memory and includes indicia for providing a visual indication of the depth of penetration of the tip of the catheter into the cystic duct.

U.S. Pat. No. 5,226,427, to Buckberg, et. al., teaches a stylet for use with a retrograde cardioplegia catheter and its methods of use. The stylet includes a stylet rod, a handle on the proximal end of the stylet rod and apredetermined curve in the distal end of the stylet rod. The handle has a thumb rest on the proximal end and a one or two finger loops extending outward from the handle. An obturator is located on the distal end of the predetermined curve to impede blood flow through a tip of the cardioplegia catheter during insertion of the catheter. The invention also contemplates methods for using the stylet.

U.S. Pat. No. 5,209,723, to Twardowski et. al., teaches a multiple lumen, intravenous catheter for hemodialysis or the like defines a distal end portion in which at least a pair of the catheter lumens each communicates with the exterior through aperturemeans. By this invention the aperture means of one of the lumens defines a first port at essentiallythe distal catheter end, and the aperture means of the other of the lumens defines a second port spaced proximally along the catheter from the distal end and first port. The second port is positioned to face radially inwardly to at least a slight degree to avoid engagement of the wall of the blood vessel that the catheter occupies. Additionally, the tip of the catheter distal of the second port is preferably of substantially helically shape, being sized to assist in keeping the second port away from the blood vessel wall. As another feature, the catheter may be angled in its as-manufactured, unstressed condition to avoid pressing by elastic memory against internal blood vessel walls. Also, the catheter may define an inflatable balloon positioned between the first and second ports as a means for spacing particularly the second port away from blood vessel walls.

U.S. Pat. No. 5,209,717, to Schmoll, et. al., teaches a method and a device for the application and the removal of locally applied active substances against solid tumors, which device consists of a catheter (1) to be positioned distally to the tumor for the collection of blood coming from the tumor, a pump (2) and a catheter (3) connected thereto and returning the blood into the body. The device is characterized in that between the two catheters (1, 3) there is present at least one container (4) capable of allowing blood to pass therethrough and containing immobilized substances having high affinity against the applied active substance.

U.S. Pat. No. 5,209,239, to Watanabe, et. al., teaches an apparatus for cystographic inspection used for observing and measuring the urethrophaxis portion and posterourethovesical angle of a patient of the acraturesis caused by a ventral pressure. The apparatus comprises a catheter, in the housing of which a flexible urethral locus indicating member, provided with a marking member, is positioned. The flexed condition of the urethral and the posterourethrovesical angle can be clearly confirmed by the urethral locus indicating member, and the position of an exterior urethral opening member, and position of an exterior urethral opening can be surely grasped by the marking member which can be roentgenographed and which is positioned on the urethral locus indicating member and that it is prevented from penetrating into the uretra and this assists in examining of the external urethral opening during roentgenography of the urethral locus indicating member of the catheter.

U.S. Pat. No. 5,167,623, to Cianci, et. al., teaches a multilumen catheter having a distal portion with a soft tip and reduced cross-section. The multilumen catheter of the present invention includes a flexible, elongated first catheter tube and a flexible, elongated, dual-lumen catheter tube which has a first and second lumens integrally formed and is disposed within the first catheter tube. The cross-section of the dual-lumen catheter tube is smaller than that of the first catheter tube and therefore, an independent, single lumen is defined in the space between the first catheter tube and the dual-lumen catheter tube. The dual-lumen catheter tube extends beyond the distal end of the first catheter tube thereby providing an overall reduced cross-section of the distal portion of the present multilumen catheter. Furthermore, the dual-lumen catheter tube may be formed from a softer material than that of the first cathether tube thereby providing a softer distal portion of the present multilumen catheter. A protective hub encapsulates and secures the proximal ends of the first and dual-lumen catheter tubes, and facilitates fluid communication between each of the lumens and fluid transfer devices.

U.S. Pat. No. 5,167,622, to Muto, a suction catheter provided with three conduits to provide th functions of suctioning, lavaging and oxygenating. The suction conduit is connected to a suction control member. The second conduit for the irrigating fluid is connected to a source of said fluid. The third conduit is connected to a source of gas under pressure. The gas conduit terminates within the irrigation conduit to form a common chamber at the distal end of the irrigation conduit from which fluid is propelled out by the pressurized gas. The gas may preferably contain oxygen.

U.S. Pat. No. 5,158,540, to Wijay, et. al., teaches a low-profile angioplasty catheter which is insertable through a guiding catheter. The angioplasty catheter has two balloons. The distal balloon dilates the stenosis. The proximal balloon is separately inflatable and selectively closes the annular passage between the angioplasty catheter and the guiding catheter. The angioplasty catheter has a central lumen with a series of openings allowing fluid communication from the central lumen into the annular passage proximally of the balloon which seals the annular passage. While the first balloon is inflated to dilate the stenosis, blood can be withdrawn from an arterial source through a lumen (or plurality thereof) in the guiding catheter and pumped into the annular passage between the angioplasty catheter and the guiding catheter. The blood then passes through the openings proximal to the proximal balloon into the central lumen of the PTCA catheter and flows beyond the distal tip of the angioplasty catheter to maintain circulation of the patient's blood at a point distal of the stenosis.

U.S. Pat. No. 5,122,115, to Marks, teaches a multiple lumen catheter specifically adapted for selective visualization of one or the other of the coronary arteries. One lumen of the multiple lumen catheter is adapted to deliver contrast agent to the coronary artery to be visualized while a second, and optionally a third, lumen is adapted to limit flow of contrast agent to one or more other locations in the aortic root complex. The invention also includes a method of preparing for coronary angiography using such a catheter.

U.S. Pat. No. 5,120,323, to Shockey, et. al., teaches a guide catheter system for use in the treatment of coronary artery disease includes a first single-lumen catheter of a relatively large internal diameter to pass a second guide catheter therethrough. The first guide catheter comprises an elongated flexible tube having a stainless steel braid embedded in the wall thereof for imparting desired torqueability characteristics to it. The first guide catheter is intended to be inserted at an appropriate point in the vascular system and then advanced until its distal end reaches the coronary ostium. The second guide catheter is fabricated by extruding a plastic, such as polyurethane thermoplastic resin over a tubular Teflon.RTM. core and because it is to be used within the lumen of the first catheter, it need not include a braided structure within its walls to prevent it from kinking. This allows the second catheter to be sufficiently slim to permit it to be advanced into a coronary artery while allowing fluids to be perfused between the outer wall of the second guide and the inner wall of the first guide catheter while still providing a sufficiently large inner lumen to pass a working catheter, e.g., an angioplasty or atherectomy catheter. An atraumatic tip is attached to the distal end of the second guide catheter.

U.S. Pat. No. 5,106,363, to Nobuyoshi, a dilation catheter defining a lumen and including a dilating member at the leading end, and a sheath defining a bore through which the dilation catheter is inserted to define a blood intake gap between the outer surface of the dilation catheter and the sheath bore and including a transverse bore branched from the sheath bore, a tube is connected at one end to the transverse bore and at another end to the lumen of the dilation catheter at a trailing end. When the sheath having the dilation catheter inserted therein is set in a blood vessel, a pump in the tube operates to take blood into the blood intake gap in the sheath, pass through the tube and the dilation catheter lumen, and feed back to the periphery of a lesion through the open leading end of the dilation catheter. The patient's own fresh blood can be injected without the need for a further cutdown or puncture for blood intake.

U.S. Pat. No. 5,102,390, to Crittenden, et. al., teaches a balloon angioplasty system includes a balloon dilatation catheter having an inflation and deflation lumen for the balloon and a main lumen extending the full length of the catheter to provide fluid communication from the proximal to the distal end of the catheter. A microdilatation probe has a small diameter and can be passed through the main lumen of the dilatation catheter. The microdilatation probe has a balloon at its distal end which is collapsible to enable it to be passed through the main lumen of the dilatation catheter so that it can be projected distally beyond the distal tip of the dilatation catheter. The probe balloon is inflatable to a diameter no smaller than the diameter of the uninflated dilatation catheter. The probe and dilatation catheter are constructed so that fluid communication is maintained through the main lumen of the dilatation catheter while the microdilatation probe extends through the catheter thereby enabling liquids to be infused and pressure measurements to be taken while the probe is in place. The probe may include a distal tip which can hold a preset curve. In use, a stenosis which cannot be crossed by the dilatation catheter may be enlarged sufficiently to permit passage of the dilatation catheter by first projecting the dilatation probe into the stenosis, then inflating the probe balloon to enlarge the lumen of the stenosis sufficiently to thereafter receive the dilatation catheter.

U.S. Pat. No. 5,084,031, to Todd, et. al., teaches a three-way double stopcock and associated tubing with which to connect both a cardioplegia solution source and a pressure monitor for the solution selectively and alternatively to either an antegrade cardioplegia catheter or a retrograde cardioplegia catheter. The stopcock includes a hollow valve body with three solution infusion ports communicating to the interior thereof in a coplanar arrangement at a first longitudinal point on the valve body. Three cardioplegia pressure monitoring ports also communicate through the valve body to the interior thereof at a second longitudinal position distinct from the first. Mounted in the valve body is a cylindrical valve core selectively rotatable about the longitudinal axis thereof between a first position in which the cardioplegia solution source and the pressure monitor are coupled to the antegrade cannula and a second position in which the cardioplegia solution source and the pressure monitor are coupled to the retrograde catheter. Formed in the valve core are a set of valving passageways for communicating with selective of the infusion ports and a set of valving passageways for communicating with selective of the pressure monitoring ports.

U.S. Pat. No. 5,021,045, to Buckberg, et. al., teaches a retrograde cardioplegia catheter and its method of use. The catheter contains two lumens, an infusion lumen through which the cardioplegic solution flows and a pressure sensing lumen for monitoring the fluid pressure at the point where the solution exits the catheter. A slightly tapered, self-filling balloon is secured to the distal end of the catheter. Also, located at the distal end of the catheter is a soft, rounded tip to prevent damage to the sensitive intimal tissues of the coronary sinus. A stylet having a predetermined curve at the distal end and a handle at the proximal end is removably located within the infusion lumen. The predetermined curve at one end of the stylet enables the cardioplegia catheter to be inserted quickly and accurately within the coronary sinus through a very small incision made in the right atrium. After the catheter is securerd in place, the stylet is withdrawn. The catheter remains in position for the duration of the operation in order to periodically readminister the cardioplegia solution.

U.S. Pat. No. 5,004,455, to Greenwood, et. al., teaches a balloon catheter which comprises a balloon catheter body, a balloon, a main passage and an auxiliary passage. The balloon is provided on the periphery of the tip portion of the catheter body to inflate for blocking a bloodstream at a desired site inside blood vessels. The auxiliary passage is provided for inflating the balloon. The main passage is provided behind the balloon, having an opening to eject a drug. The tip portion of the balloon catheter is inserted into one of branches of the blood vessel near targeted affected part. A fluid is injected into the balloon so that the balloon blocks a bloodstream in the branches. Therefore, a drug is ejected through the main passage of the balloon catheter into other branches.

U.S. Pat. No. 4,883,459, to Calderon, teaches the study of tumors in the body of a patient in situ by a monitor, such as computer assisted tomography, X-ray or the like, while optimal flow paths through the tumor area are established. A catheter with a suction lumen and an infusion lumen, with seals associated with each, is placed in the patient's vein near the tumor. Flow is then sealed in the vein with the infusion seal. A carrier medium dye is injected into the tumor at selected flow rates and differential pressures. Flow of the dye through the tumor is observed on the monitor to determine optimal retrograde perfusion paths through the tumor for the selected flow rates and differential pressures. Once the optimal perfusion paths are noted, a preferential attack area in the tumor is located using a different, less dense carrier dye and increased fluid back pressure in the infusion system. Once the attack area in the tumor is located, microspheres with active ingredients, such as chemotherapy, can be selectively perfused through one of the paths in the tumor to the attack site and forced into the tumor, once at the attack site, using increased back pressure. The process may be cyclically repeated using the same or different active ingredients. The procedure may be repeated through the tumor in different paths and attack points at desired active ingredient dosages using increased back pressures.

U.S. Pat. No. 4,867,742, to Calderon, teaches the study of tumors in the body of a patient in situ by a monitor, such as computer assisted tomography, X-ray or the like, while optimal flow paths through the tumor area are established. A catheter with a suction lumen and an infusion lumen, with seals associated with each, is placed in the patient's vein near the tumor. Flow is then sealed in the vein with the infusion seal. A carrier medium dye is injected into the tumor at selected flow rates and differential pressures. Flow of the dye through the tumor is observed on the monitor to determine optimal retrograde perfusion paths through the tumor for the selected flow rates and differential pressures. Once the optimal perfusion paths are noted, microspheres with active ingredients, such as chemotherapy, can be selectively perfused through each of the paths in the tumor at desired flow rates, pressures and active ingredient dosages. Alternatively, microspheres with different active ingredients can be selectively introduced through the tumor in different paths at desired active ingredient dosages and established flow rates and pressures.

U.S. Pat. No. 4,820,261, to Schmoll, et. al., a device for the removal of active substances locally applied against solid tumors consists of a catheter (1) to be positioned distally to the tumor for the collection of blood coming from the tumor, a pump (2) and a catheter (3) connected thereto and returning the blood into the body. The device is characterized in that between the two catheters (1, 3) there is present at least one container (4) capable of allowing blood to pass therethrough and containing immobilized antibodies against the applied active substance.

U.S. Pat. No. 4,714,460, to Calderon, teaches catheter feedback methods and systems for optimizing the infusion of a drug, such as a chemotherapeutic agent via retrograde perfusion through the venous side of the vascular network to a selectively determined portion of a solid tumor. Monitoring and regulatory capability are provided for controlling the outflow of the drug and thereby for controlling the dose rate, the duration of exposure of the drug, the leakage factor, and the level of systemic toxicity, all critical factors in the successful treatment of solid tumors. A feedback loop for practicing the method comprises two concentric balloon catheters capable of extensive maneuvering and selective placement within the venous drainage of the vascular system, creating a third in-vivo space for repeated perfusion of the selected portion of a diseased organ as often as desired, providing maximum exposure of the chemotherapy to the tumor with minimum exposure to any other portions of the patient's body.

It is well known that blood is primarily fed to a pelvic tumor by way of the iliac artery, and primarily withdrawn by way of the iliac vein. Prior art apparatuses and processes similar to the instant invention, have been for the most part taylored to tumors occurring in various organs, i.e., most particularly, the liver, which have well defined feed arteries and veins. Despite the plethora of such prior art apparatuses and processes, there has hitherto been no effective manner to apply them to localized tumors occurring in the pelvic cavity of a patient inflicted with, i.e., cancer. Thus there has been a long felt need for an apparatus and process for treating localized tumors occurring in the pelvic cavity of a patient inflicted with cancer.

SUMMARY OF THE INVENTION

It is the primary object of the instant invention to accomodate the long felt need for an apparatus and process for treating localized tumors occurring in the pelvic cavity of a patient inflicted with cancer.

The instant invention in large part solves the problems of the prior and fulfills a long felt need by providing a novel apparatus and process.

The instant invention provides a novel catheter for use in the treatment of tumors which occur in the pelvic cavity of a patient.

The instant invention provides a novel method of using a catheter for use in the treatment of tumors which occur in the pelvic cavity of a patient.

The instant invention provides a novel catheter and a novel method of its use in the treatment of tumors which occur in the pelvic cavity of a patient.

The instant invention provides a novel kit which includes a novel catheter and a novel method of its use in the treatment of tumors which occur in the pelvic cavity of a patient inflicted with cancer.

Here are the more important features of the invention as broadly outlined, in order that the detailed description that follows may be better understood; and in order for the present contribution to the art may be better appreciated. There are additional features of the invention that will be described hereinafter and which form the subject matter of the appended claims. Those of ordinary skill in the art will appreciate that the conception upon which this disclosure is based may readily be utilized as a basis for the designing of other structures, methods and systems for carrying out the several purposes of the instant invention. It is important, therefore, that the claims be regarded as including such equivalent constructions insofar as they do not depart from the spirit and scope of the instant invention.

Further, the purpose of the instant abstract is to enable the U.S. Patent and Trademark office and the public generally, and especially the scientists, engineers and practitioners in the art who are not familiar with patent or legal terms or phraseology, to determine quickly from a cursory inspection of it, the technical disclosure of the patent application. The abstract is neither intended to define the invention of the instant patent application, which is measured by the claims, nor is it intended in any manner to be limiting as to the scope of the instant invention.

In light of the foregoing, it is therefore an object of the instant invention to provide a new and improved apparatus and process which has all of the advantages of the prior art and none of its disadvantages.

It is another object of the instant invention to provide a new and improved apparatus and process which may be easily and efficiently manufactured and marketed.

It is another object of the instant invention to provide a new and improved apparatus which is of a durable and reliable construction.

It is another object of the instant invention to provide a new and improved apparatus which can be manufactured at correspondingly lower cost with regard to both labor and materials, and which accordingly can be sold at a correspondingly lower cost, thus promoting commerce.

It is a further object of the instant invention to provide a new and improved apparatus and method which provides at least some of the advantages of the prior art schemes, while simultaneously eliminating at least some of the disadvantages of them.

It is a further object of the instant invention to provide a new and improved apparatus and process which is particularly designed for accommodating the treatment of tumors occurring in the pelvic cavity of a patient inflicted with cancer.

Other objects, features, and advantages of the instant invention, in its details of construction and arrangement of parts, will be seen from the above, from the following description of the preferred embodiment when considered in light of the drawings and the appended claims.

BRIEF DESCRIPTION OF THE DRAWINGS

FIG. 3 depicts a partial cross-sectional side view of a first alternative embodiment of a double balloon catheter as contemplated by the invention.

FIG. 4 shows a cross-sectional end view of the shaft of the double balloon catheter of FIG. 3.

FIG. 5 shows a cross-sectional end view of the midsection of a modification of the double balloon catheter of FIG. 3.

FIG. 8 shows a cutaway cross-sectional side view of the interior of a double balloon catheter encompassed by the invention.

DETAILED DESCRIPTION OF THE INVENTION

Figure 1:
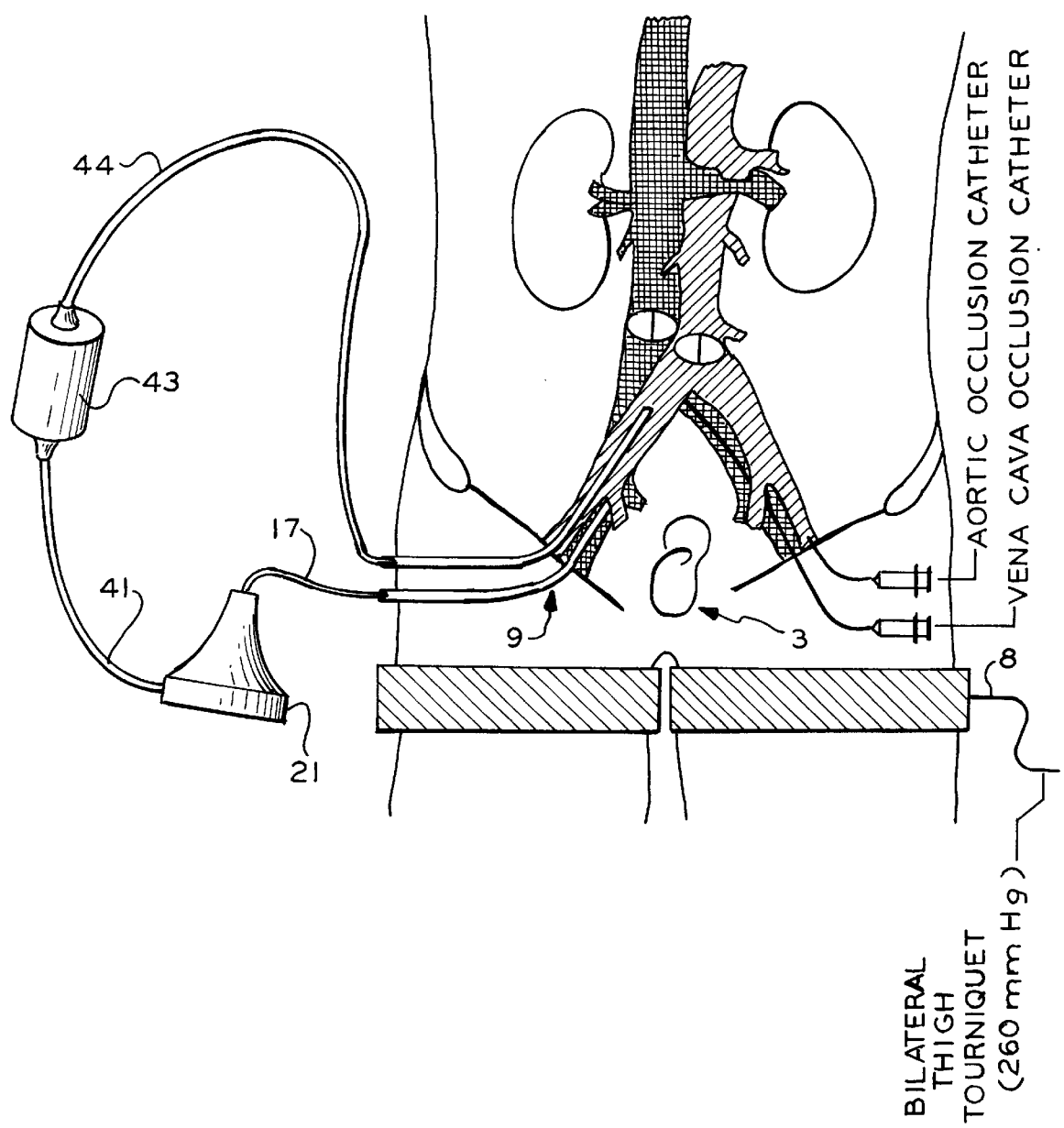
FIG. 1 depicts the basic apparatus of the invention as shown in relationship the pelvic cavity of the body of a patient.

FIG. 1, shows the basic apparatus used to practice the process of the instant invention in relationship to the pelvic cavity of a patient. The instant invention is primarily applicable to tumors located in the pelvic cavity which are fed by blood from the aorta and from which blood is discharged to the vena cava. The invention is practiced by creating a localized fluid circuit which isolates the tumor for maximum recycle of a chemotherapeutic agent therethrough, while minimizing flow of the agent through the heathy tissues surrounding the tumor 3. The blood flow path to the patient's heart via the iliac vein is isolated by a common iliac catheter 9 and bilateral thigh tourniquets 8. Tumor 3 located within the thusly isolated circuit is thereafter infused with chemotherapeutic drugs via aortic occlusion catheter 4 and vena cava occlusion catheter 3. The blood passing through the aorta and vena cava is infused with concentrations of a chemotherapeutic agent lethal to the cancer cells of the tumor 3 via aortic occlusion catheter 4 and vena cava catheter 3. The thusly infused blood is passed via the common iliac vein to the common iliac vein catheter 9, typically a double balloon catheter. The balloons of the double balloon catheter 9 are positioned central and peripheral of the common iliac vein. The balloons are critically designed, sized and spaced such that after inflation, they can accommodate the geometric constrains of the patient's common iliac vein, thus isolating substantially all of the outflow blood from the tumor 3. Substantially all of the contaminated blood is passed through the double balloon catheter to tubing 17 to a point exterior to the body 2, to a pump 21. Typical of such a pump is a Bio Medicus BP-50 Bio-Pump having a priming volume of 48 ml, containing two rotator cones and providing a maximum flow rate of 5 liters per minute. Pump 21 passes the blood through the extracorporeal circuit at relatively constant low pressure. The purpose in doing so is to avoid raising or lowering the fluid pressure of the total circuit ranging from the blood vessel through the return to the body. The contaminated blood is thereafter passed through tubing 41 into detoxification zone 43. Typical of such a detoxifiction zone is a hemoperfusion cartridge containing activated carbon. Suitable cartridge systems are obtainable from Clark Research and Development, Inc., New Orleans, La. 70121 and from Gambro Dialysatoren KG, d-7450 Hechingen, Federal Republic of Germany AUT 224 (sold under the trademark of ADSORBA.RTM.). The detoxified blood is passed through tube 44 and infused back into the body of the patient through the common iliac artery via catheter 69.

Figure 2:
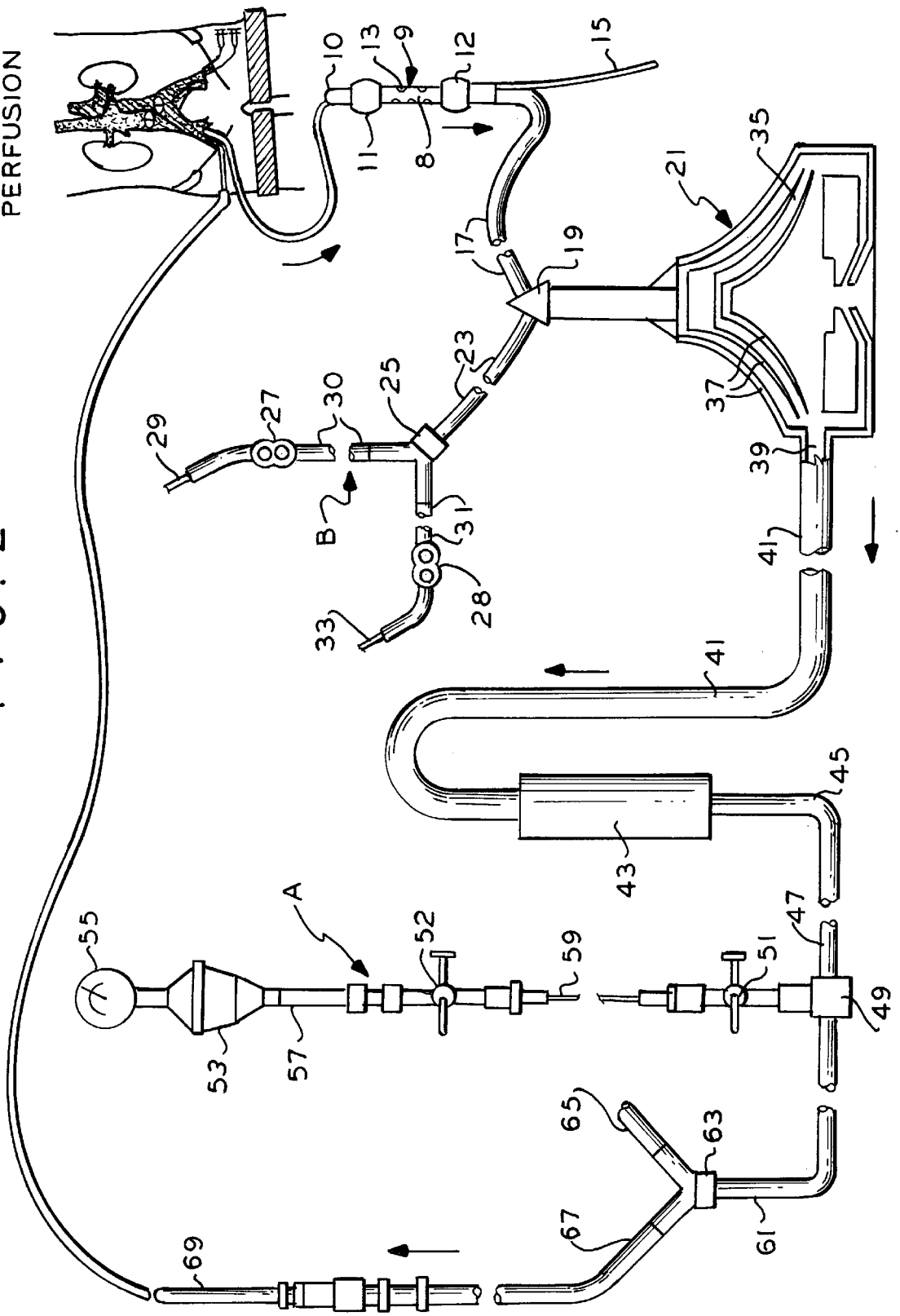
FIG. 2 depicts a diagrammatic of an apparatus assembly for carrying out the process of the invention.

FIG. 2 shows the schematic relationship between the isolated circuit within the pelvic cavity, the iliac vein catheter 9, through which toxified blood is passed from the tumor and the common iliac artery catheter 69 through which detoxified blood is infused back into the iliac artery. Double balloon catheter 9 typically comprises central balloon 11 and peripheral balloon 12, each injuxtaposition to cylindrical fenestration zone 8. Zone 8 contains fenestrations 13 sufficient in total area to allow the complete removal of the toxified blood flow from the tumor into the catheter 9. The hollow interior (main lumen) of catheter 9 is of sufficient size to completely remove the blood from the blood vessel without elevating blood pressure. Catheter 9 is provided with channel 15 that is used to inject fluid into the balloons 11 and 12 for inflation or to withdraw fluids for deflation. The venous flow is passed through catheter 9 into openly connected tube 17. Tube 17 may be interrupted by a pressure monitor the same as assembly A, discussed below, that is later provided in the extracorporeal circuit. Tube 17 may alternatively be connected directly with pump 21 or to Y-fitting 19, as shown. Also connected to Y-fitting 19 is ancillary feed system B comprising tube 23, Y-fitting 25, and multiple IV spikes 29 and 33 each connected to tubes 30 and 31 respectively, and each is provided with a clamp, 27 and 28, respectively. These lines can be used for the introduction of medications as required.

Typically, pump 21 is a smooth rotator pump design and a particularly desirable pump is a Bio Medicus BP-50 Bio-Pump having a priming volume of 48 ml, containing two rotator cones and providing a maximum flow rate of 5 liters per minute. The contaminated blood is gently pushed between the smooth rotators 37 in zones 35 and issued from the pump through port 39 into tube 41. Tube 41 is connected to cartridge or canister 43 containing a meshed sack of activated carbon particles coated with an acrylic resin containing heparin, see Clark, supra. The outflow from cartridge 43 is fed to tube 45 and then to tube 47 that is connected to pressure monitoring assembly A. Pressure monitoring assembly A comprises a pressure monitor gauge 55 connected to fluid membrane vessel 53 that contains a thin membrane that separates the gauge 55 from the blood in vessel 53 and responds to the fluid pressure of the blood in vessel 53. That response is read by the gauge. Vessel 53 is connected to tubing 57, that is connected to stopcock 52. Stopcock 52 is connected to flexible tubing 59 that in turn is connected to stopcock 51, the latter secured in fitting 49.

Blood from tubing 47 is passed to Y-connector 63 via tubing 61, then to tubings 65 and 67. Tubings 65 and 67 are each connected to catheter 69 and another catheter (connected to tube 65) not shown. These catheters are provided for returning the purified blood to the subclavian veins.

FIG. 3 depicts a double balloon catheter design typically having up to a 24 French (Fr) O.D. Zone 100 is provided with slotted fenestrations 104 in the solid plastic tubing 102. The open end 118 terminates the catheter. End 118 is tapered to the caliber of an angiographic guide wire that will, under fluoroscope control, allow the catheter to be advanced from the femoral vein to the proper location in the inferior vena cava without risk of injury to the interior of the vessels. Appropriate guide wires may be, for example, 0.035, 0.038, or 0.045 inch in diameter. During treatment, the catheter end hole is closed using a standard angiographic apparatus (tip-occluding wire), that consists of a thin wire long enough to traverse the length of the catheter at the end of which is a stainless steel bead just large enough to obstruct the catheter's end-hole when advanced into it (similar to a metal stopper that closes the outlet from a sink when advanced).

Alteratively, the end hole can be made 7–12 Fr in diameter in order to accommodate a return catheter. The return catheter can be used to return treated blood to the systemic circulation. The return catheter is advanced over a guide wire through the main lumen of the double balloon catheter and through the end hole 118 into the right atrium or superior vena cava. The return catheter can be made to gradually taper its O.D. by decreasing its wall thickness, leaving the I.D. constant, since the location of the tip of the return catheter is not critical. The length over which the catheter tapers is arbitrary. The taper is constructed so that the tip of the catheter is its narrowest O.D. and the O.D. increases toward the femoral vein. As this return catheter is advanced through the lumen of the main catheter the tip easily passes through the end hole 118 of the double balloon catheter. The tapered end of the return catheter is advanced until it obstructs the end hole 118, preventing systemic blood from entering the double balloon catheter when the balloons are inflated but leaving an open lumen through the return catheter to return blood beyond the isolated venous segment without mixing with contaminated blood.

The catheter tubing (body) can be made of a variety of plastic materials such as polypropylene, polyethylene, polyvinylchloride, ethylene vinylacetate copolymers, polytetrafluoroethylene, polyurethane, and the like. A favorable plastic combination for catheters containing a return lumen are a homogeneous mixture of high density polyethylene and linear low density polyethylene. That combination gives favorable stiffness at ambient conditions and allows the use of especially thin wall thicknesses. When the surface of the catheter is made of a plastic that is difficult to bond with a balloon, the plastic may be treated first by one or more of a number of well known methods that make bonding possible. The methods include plasma treatment, ozone treatment, and the like. Balloons 110 and 114 may be made from a plurality of elastomeric materials such as latex rubber, polyurethanes, spandex type polyurethanes, EPDM rubber, and the like. The balloons are typically adhesively bonded at sheath surfaces 108 and 112, respectively. A wide variety of adhesives may be employed. Polyacrylonitrile type adhesives, rubber latex adhesives and the like may be used to secure the balloon to the sheath surfaces 108 and 112.

FIG. 4 depicts a cross section of a typical catheterdesign such as that shown in FIG. 3. The interior of the catheter contains main lumen 120 and 4 additional lumina 124 molded into the outer wall 122. The additional lumina can be used for the various functions described above.

FIG. 5 depicts a cross section of an alternate embodiment of the catheter of the instant invention similar to that shown in FIG. 3 but containing only three lumina. The interior of the catheter contains main lumen 130 and two supplementary lumina 131 molded into segment 133 of wall 135. The supplementary lumina can be used for the various functions described above.

Figure 6:
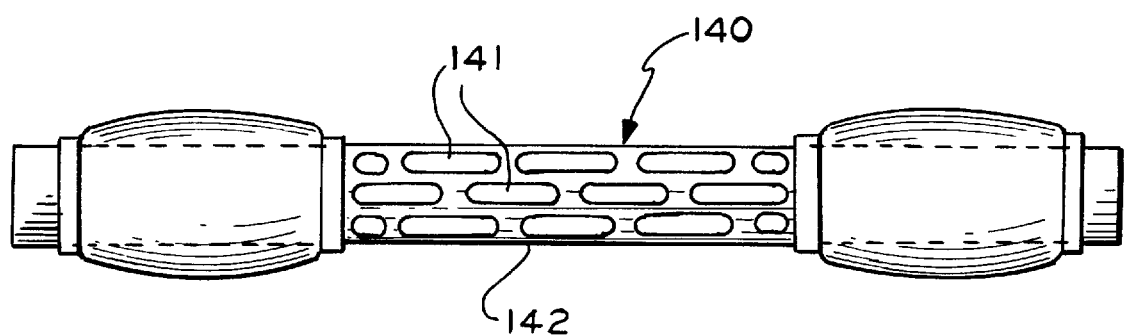
FIG. 6 shows a partial cross-sectional side view of another design of double balloon catheter useful in the process of the invention.

FIG. 6 depicts yet another alternate embodiement of the double balloon catheter of the instant invention, which can have an outside diameter of 24 French such as in the fenestration zone 140 and an inside diameter of less than 22 Fr. Zone 140 is provided with slotted fenestrations 141 in the plastic tubing 142.

Figure 7:
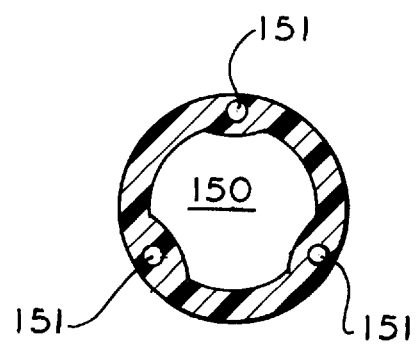
FIG. 7 shows a cross-sectional end view of the shaft of the double balloon catheter of FIG. 6.

FIG. 7 depicts a cross sectional view of still yet another embodiment of the catheter of the instant invention showing a main lumen 150 and 3 supplemental lumina 151.

FIG. 8 provides a more detailed schematic cross sectional side view of a typical double balloon catheter 161. In this depiction, the catheter sidewall 163 is penetrated by a plurality of fenestrations 165. The main lumen 169 contains at its periphery supplemental lumina 170, 171 and 173. Supplemental lumen 170 can be used to accommodate a guidewire, supplemental lumen 171 can be used to accommodate a pressure monitor, and supplemental lumen 173 is used to supply fluid to the balloons 166 and 167 through openings 175 and 177.

The bilateral thigh tourniquets 8 are critical for resticting the flow of blood in the pelvic cavity at a point at within the pelvic cavity, opposite the heart of said patient relative to said tumor.

Prior to the instant invention, no effective or practical method and/or apparatus existed for for the treatment of tumors which occurred in an extremity, such as the arm or leg of a patient. Thus, common to all of the double balloon catheter embodiments of the instant invention is the critical "customized" sizing and spacing of the respective elements thereof, in accomodation to the varied sizes and dimensions of: the particular tumor to be treated, and the blood vessel which withdraws the blood therefrom.

The term "tumor," as used herein, also spelled TUMOUR, also called NEOPLASM, a mass of abnormal tissue that arises without obvious cause from preexisting body cells, has no purposeful function, and is characterized by a tendency to autonomous and unrestrained growth. Tumors are quite different from inflammatory or other swellings because the cells in tumors are abnormal in their appearance and other characteristics. Abnormal cells—the kind that generally make up tumors—differ from normal cells in having undergone one or more of the following alterations: (1) hypertrophy, or an increase in the size of individual cells; this feature is occasionally encountered in tumors but occurs commonly in other conditions; (2) hyperplasia, or an increase in the number of cells within a given zone; in some instances it may constitute the only criterion of tumor formation; (3) anaplasia, or a regression of the physical characteristics of a cell toward a more primitive or undifferentiated type; this is an almost constant feature of malignant tumors, though it occurs in other instances both in health and in disease.

The term "cancer," as used herein refers to any one of a group of more than 100 related diseases characterized by the uncontrolled multiplication of abnormal cells in the body. If this multiplication of cells occurs within a vital organ or tissue, normal function will be impaired or halted, with possible fatal results. Tumors, which primarily occur with the advent of cancer, are classified as malignant or benign; intermediary forms exist, however, and benign bone tumor may present therapeutic problems because of its location. Primary bone tumors are characterized by their origin in the skeletal tissue elements, for example, bone tissue tumors (the malignant osteogenic sarcoma and the benign osteoma), cartilage tumors (the malignant chondrosarcoma and the benign chondroma), bone marrow tumors (the malignant myeloma and the benign eosinophilic granuloma). Metastatic (secondary) tumors are malignant by definition and are characterized by their site of origin Typically, tumors occurring in an extemety occur in the form of, i.e., a bone lesion. A bone leasion is a malignant growth of the bone caused by metastatic spread from cancer in other organs. Primary bone cancer is fairly uncommon, but bone lesions from metastases are seen in more than half of all cancer patients at the time of death. There are two types of metastatic bone lesion: osteoblastic, in which new bone is laid down in a disorganized fashion, and osteolytic, in which bone is destroyed, causing fractures and deep bone pain. Lung, breast, kidney, and prostate cancers are the primary tumors that most commonly cause bone lesions; lung cancer causes a typical punched-out lytic lesion while breast and prostate tumors more often produce osteoblastic metastases. Bone lesions commonly occur in the vertebral column, ribs, and pelvis, as well as in the long bones of the arms and legs.

The occurrence of papillomatous tumors of the renal pelvis has already been mentioned. Similar tumors in the lower urinary tract give rise to painless hematuria. Workers with the chemicals naphthyl amine and benzidine have a high incidence of bladder tumors, often multiple and recurrent. Blood in the urine is the most frequent symptom, but bladder irritation with difficulty in urination appears later. Removal when practicable or destruction by diathermy are normal treatments.

X-ray examination of any part of the urinary tract after introduction of a radiopaque substance (often an organic iodine derivative) that casts an X-ray shadow. This contrast fluid, which passes quickly into the urine, may be taken orally or injected intravenously. It may also be injected directly into the area being examined. Tumors, tuberculous abscesses, kidney stones, and obstruction by prostatic enlargement may be detected by this method. Specific types of urography include pyelography (examination of the kidney and ureter) and cystography (examination of the bladder). Motion-picture "voiding cystograms" provide evidence of gross reflux of urine into the ureters and pelvis of the kidney during voiding. Imaging techniques are used to determine the anatomical site, configuration, and level of functioning of the kidneys, pelvis, and ureters. A plain X ray nearly always precedes any other more elaborate investigation, so that the size, outline, and position of the two kidneys, as well as information about the presence or absence of calcium-containing renal stones or zones of calcification can be ascertained. Excretion urography is one of the simplest methods of defining these aspects more precisely, though this radiological method is giving way to noninvasive imaging methods such as ultrasonography and nuclear magnetic resonance (NMR). In excretion urography, the kidneys are observed in X rays after intravenous injection of a radiopaque iodine-containing compound that is excreted largely by glomerular filtration within one hour of the injection. A series of X-ray images (nephrograms) then indicates when the contrast substance first appears and reveals the increasing radiographic density of the renal tissue. The X rays also indicate the position, size, and presence of scarring or tumors in the organs and provide an approximate comparison of function in the two kidneys. Finally the dye collects in the bladder, revealing any rupture or tumor in this organ.

Multiple myeloma, also called PLASMA CELL MYELOMA, or MYELOMATOSIS, common malignant tumor in the bone marrow, usually occurring in middle age and later. It is slightly more common in males and affects mostly the flat bones typically in the pelvis. The disease occurs when B lymphocytes or their precursors multiply into clones of cancerous plasma cells that produce massive amounts of antibody proteins. This antibody, called myeloma protein (q.v.), has no infection-fighting capability and displaces most healthy antibody in the blood. It can collect in the tubules of the kidney and cause renal failure. Bone destruction also frees calcium into the circulation, which may be redeposited in abnormal places, such as the kidney. Symptoms and signs include pain, anemia, weakness, a tendency to hemorrhage, and kidney insufficiency. Pathological bone fractures occur, and neurological symptoms may follow the collapse of affected vertebrae. The disease is progressive, and most patients die within three years of diagnosis. In the presence of multiple lesions, only symptomatic treatment is possible; when only one lesion is present, surgery or irradiation may arrest or cure the disease.

The term "detoxification," and its variants, as used herein, includes, but is not necessarily limited to: cascade membrane plasmapheresis, hemodialysis, hemoperfusion, membrane plasmapheresis, peritoneal dialysis, single-needle dialysis, hemosoption, hemoperfusion, regular peritoneal dialysis, recirculating peritoneal dialysis, continuous ambulatory peritoneal dialysis (CAPD), hemoultrafiltration, hemofiltration, blood centrifugation, and the like.

The invention is applicable to muscle tumors. Muscle tumors are abnormal tissue growth located in or originating from muscle tissue. Tumors may either arise in muscle tissue or spread to it. Three major tumor types may appear; they are known as leiomyomas, rhabdomyomas, and rhabdomyosarcomas.

The invention is also particularly useful in treating i.e., osteoclastoma also called GIANT-CELL Tumor OF BONE, a bone tumor found predominantly in the knee region, but also occurring in the wrist, hand, foot, arm, and pelvis. The giant cells (large, often multinucleated cells) found in these tumors resemble osteoclasts, for which the tumor is inappropriately named. Usually seen in young adults between the ages of 20 and 40, this relatively uncommon, painful tumor is considered potentially malignant. Most tumors are benign at the outset and are removed by curettage (scraping). Unfortunately, about 50 percent of the tumors removed in this way recur, of which a small percentage spread to other parts of the body (metastasize). Until now, this has prompted some physicians to recommend more aggressive treatment, such as complete excision or amputation.

The term "means"[and its variants], as used herein, means: any and/or all equivalent structure which when manipulated, will render the claimed function.

The term "process" or "method" [and its variants] as used herein, means: (1): a natural phenomenon marked by gradual changes that lead toward a particular result (2): a natural continuing activity or function; or, a series of actions or operations conducing to an end; or, especially: a continuous operation or treatment especially in manufacture.

Although the invention has been described with reference to certain preferred embodiments, it will be appreciated that many variations and modifications may be made within the scope of the broad principles of the invention. Hence, it is intended that the preferred embodiments and all of such variations and modifications be included within the scope and spirit of the invention, as defined by the following claims.

I claim:

1. Apparatus for isolated perfusion of the pelvic cavity of a patient comprising:
    a first catheter designed, sized and dimensioned for occluding the aorta of said patient;
    a second catheter designed, sized and dimensioned for occluding the vena cava of said patient;
    a third catheter designed, sized and dimensioned for occluding the common iliac vein of said patient;
    a fourth catheter designed, sized and dimensioned for returning detoxified blood to the common iliac artery of said patient;
    a pump having a suction port and a discharge port;
    a first conduit for providing fluid communication between said third catheter and said suction port;
    a detoxification device having an inlet and an outlet;
    a second conduit for providing fluid communication between said discharge port and said inlet;
    a third conduit for providing fluid communication between said outlet and said fourth catheter; and,
    bilateral thigh tourniquets for restricting the flow of blood between the legs and said pelvic cavity of said patient.

2. The apparatus of claim 1, wherein said third catheter further comprises structure for percutaneous insertion into said common iliac vein, including (a) a plastic tube having a cranial end and a caudal end, said plastic tube defining a main lumen for outflowing blood, two balloons, fixedly spaced apart about said plastic tube and bonded thereto for inflation thereabout, one being contiguous to said cranial end;
    wherein said balloons are sized and spaced on said plastic tube sufficient, that when inflated, they have sufficient size and spacing therebetween to substantially block the flow of blood in said common iliac vein and to substantially isolate outflow from said tumor to other portions of said common iliac vein;
    fenestration in said plastic tube between said balloons to said main lumen;
    second and third lumina within said plastic tube;
    said second lumen connecting to one of said balloons; and,
    said third lumen connecting to the other of said balloons for effecting inflation or deflation of said balloons;
    said cranial end of said plastic tube being closed to substantially all inflow of blood; and,
    a return catheter for returning blood removed through said main lumen to the patient.

3. The apparatus of claim 2 wherein said plastic tube has a fourth lumen sized to accommodate an angiographic guide wire.

4. The apparatus of claim 2 wherein said second and third lumina connect and are common to the interiors of said balloons.

5. The apparatus of claim 2 wherein said second and third lumina lie within the wall of said plastic tube.

6. A kit comprising:
    a first catheter designed, sized and dimensioned for occluding the aorta of said patient;
    a second catheter designed, sized and dimensioned for occluding the vena cava of said patient;
    a third catheter designed, sized and dimensioned for occluding the common iliac vein of said patient;
    wherein said third catheter further comprises structure for percutaneous insertion into said common iliac vein, including (a) a plastic tube having a cranial end and a caudal end, said plastic tube defining a main lumen for outflowing blood, two balloons, fixedly spaced apart about said plastic tube and bonded thereto for inflation thereabout, one being contiguous to said cranial end;
    wherein said balloons are sized and spaced on said plastic tube sufficient, that when inflated, they have sufficient size and spacing therebetween to substantially block the flow of blood in said common iliac vein and to substantially isolate outflow from said tumor to other portions of said common iliac vein; fenestration in said plastic tube between said balloons to said main lumen;
    second and third lumina within said plastic tube;
    said second lumen connecting to one of said balloons; and,
    said third lumen connecting to the other of said balloons for effecting inflation or deflation of said balloons;
    said cranial end of said plastic tube being closed to substantially all inflow of blood; and,
    a return catheter for returning blood removed through said main lumen to the patient;
    a fourth catheter designed, sized and dimensioned for returning detoxified blood to the common iliac artery of said patient;
    a pump having a suction port and a discharge port;
    a first conduit for providing fluid communication between said third catheter and said suction port;
    a detoxification device having an inlet and an outlet;
    a second conduit for providing fluid communication between said discharge port and said inlet;
    a third conduit for providing fluid communication between said outlet and said fourth catheter; and,
    bilateral thigh tourniquets for restricting the flow of blood between the legs and said pelvic cavity of said patient.

7. The kit of claim 6 wherein the detoxification device includes a device selected from the group consisting of devices designed to provide hemoperfusion, hemodialysis, hemofiltration and hemoabsorption.

8. The kit of claim 6 wherein said second catheter is designed to fit within said plastic tube and said cranial end tapers are designed to fit thereabout such that the treated blood is returned past the cranial balloon and said kit includes arterial injection means for introducing said treating agent into a common iliac vein leading to said tumor.

9. The kit of claim 6 wherein said treating agent is an anti-cancer agent.

10. The kit of claim 6 further including an angiographic guide wire, wherein said cranial end is tapered to a diameter of an angiographic guide wire.

11. A method for isolated pelvic perfusion comprising the steps of:
 providing a kit which includes a first catheter designed, sized and dimensioned for occluding the aorta of said patient; a second catheter designed, sized and dimensioned for occluding the vena cava of said patient; a third catheter designed, sized and dimensioned for occluding the common iliac vein of said patient; a fourth catheter designed, sized and dimensioned for returning detoxified blood to the common iliac artery of said patient; a pump having a suction port and a discharge port; a first conduit for providing fluid communication between said third catheter and said suction port; a detoxification device having an inlet and an outlet; a second conduit for providing fluid communication between said discharge port and said inlet; a third conduit for providing fluid communication between said outlet and said fourth catheter; and, bilateral thigh tourniquets for restricting the flow of blood between the legs and said pelvic cavity of said patient;
 occluding said aorta with said first catheter;
 occluding said vena cava with said second catheter;
 occluding said common iliac vein with said third catheter;
 occluding said common iliac artery with said fourth catheter;
 restricting said flow of blood with said bilateral thigh tourniquets;
 perfusing chemotherapeutic agents into the pelvic cavity through said first and second catheters;
 withdrawing toxified blood from said pelvic cavity through said third catheter;
 detoxifying said toxified blood with said detoxification device to provide detoxified blood; and,
 reinfusing said detoxified blood through said fourth catheter.

12. Apparatus for isolated perfusion of the pelvic cavity of a patient comprising:
 a first catheter designed, sized and dimensioned for occluding the aorta of said patient;
 a second catheter designed, sized and dimensioned for occluding the vena cava of said patient;
 a third catheter designed, sized and dimensioned for occluding the common iliac vein of said patient;
 a fourth catheter designed, sized and dimensioned for returning detoxified blood to the common iliac artery of said patient;
 a pump having a suction port and a discharge port; a first conduit for providing fluid communication between said third catheter and said suction port;
 a detoxification device having an inlet and an outlet;
 a second conduit for providing fluid communication between said discharge port and said inlet;
 a third conduit for providing fluid communication between said outlet and said fourth catheter;
 bilateral thigh tourniquets for restricting the flow of blood between the legs and said pelvic cavity of said patient;
 said third catheter further comprises structure for percutaneous insertion into said common iliac vein, including (a) a plastic tube having a cranial end and a caudal end, said plastic tube defining a main lumen for outflowing blood, two balloons, fixedly spaced apart about said plastic tube and bonded thereto for inflation thereabout, one being contiguous to said cranial end;
 wherein said balloons are sized and spaced on said plastic tube sufficient, that when inflated, they have sufficient size and spacing therebetween to substantially block the flow of blood in said common iliac vein and to substantially isolate outflow from said tumor to other portions of said common iliac vein;
 fenestration in said plastic tube between said balloons to said main lumen;
  second and third lumina within said plastic tube;
  said second lumen connecting to one of said balloons; and,
 said third lumen connecting to the other of said balloons for effecting inflation or deflation of said balloons;
 said cranial end of said plastic tube being closed to substantially all inflow of blood;
 a return catheter for returning blood removed through said main lumen to the patient; and
 said cranial end is tapered to a diameter of an angiographic guide wire.

* * * * *